United States Patent
Hindi

(10) Patent No.: US 11,242,410 B1
(45) Date of Patent: *Feb. 8, 2022

(54) URCHIN-SHAPED NANOCRYSTALLINE MATERIAL

(71) Applicant: King Abdulaziz University, Jeddah (SA)

(72) Inventor: Sherif Shawki Zaki Hindi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/510,992

(22) Filed: Oct. 26, 2021

Related U.S. Application Data

(60) Continuation of application No. 17/021,066, filed on Sep. 15, 2020, now Pat. No. 11,161,918, which is a division of application No. 16/137,898, filed on Sep. 21, 2018, now Pat. No. 10,808,045.

(51) Int. Cl.
*C08B 15/02* (2006.01)
*C12M 1/00* (2006.01)
*C12M 1/06* (2006.01)

(52) U.S. Cl.
CPC .......... *C08B 15/02* (2013.01); *C12M 27/02* (2013.01); *C12M 45/06* (2013.01)

(58) Field of Classification Search
None
See application file for complete search history.

(56) References Cited

U.S. PATENT DOCUMENTS

2017/0291962 A1   10/2017   Hindi et al.

FOREIGN PATENT DOCUMENTS

| CN | 104629077 A | 5/2015 |
|---|---|---|
| CN | 102966002 B | 7/2015 |
| CN | 103044871 B | 8/2015 |
| CN | 105699559 A | 6/2016 |
| CN | 105754155 A | 7/2016 |
| CN | 106220904 A | 12/2016 |
| EP | 3 202 978 A1 | 8/2017 |

OTHER PUBLICATIONS

Daniel Bondeson, et al., "Optimization of the isolation of nanocrystals from microcrystalline cellulose by acid hydrolysis", Springer Link, Apr. 5, 2006, p. 1.

Michael Ioelovich, "Study of Cellulose Interaction with Concentrated Solutions of Sulfuric Acid", International Scholarly Research Network Chemical Engineering, vol. 2012, 2012, pp. 1-7.

Lanxing Du, et al., "Preparation and Characterization of Cellulose Nanocrystals from the Bio-ethanol Residuals", Nanomaterials, vol. 7, No. 51, 2017, pp. 1-12.

Ping Lu, et al., "Preparation and properties of cellulose nanocrystals" Rods, spheres, and network, Carbohydrate Polymers, vol. 82, 2010, pp. 329-336.

*Primary Examiner* — Dale R Miller
(74) *Attorney, Agent, or Firm* — Oblon, McClelland, Maier & Neustadt, L.L.P.

(57) ABSTRACT

The invention is directed to a simple and economical method for producing nanocrystalline cellulose from microcrystalline cellulose by contacting frozen concentrated sulfuric acid with microcrystalline cellulose, diluting the mixture in water and hair-shaped ice to hydrolyze the microcrystalline cellulose, and separating the NCC. Another aspect of the invention pertains to an apparatus for conducting this method which includes an acid resistant hydrolysis container having a cooling jacket containing a hollow stirrer each of which may be filled with liquid nitrogen.

16 Claims, 8 Drawing Sheets

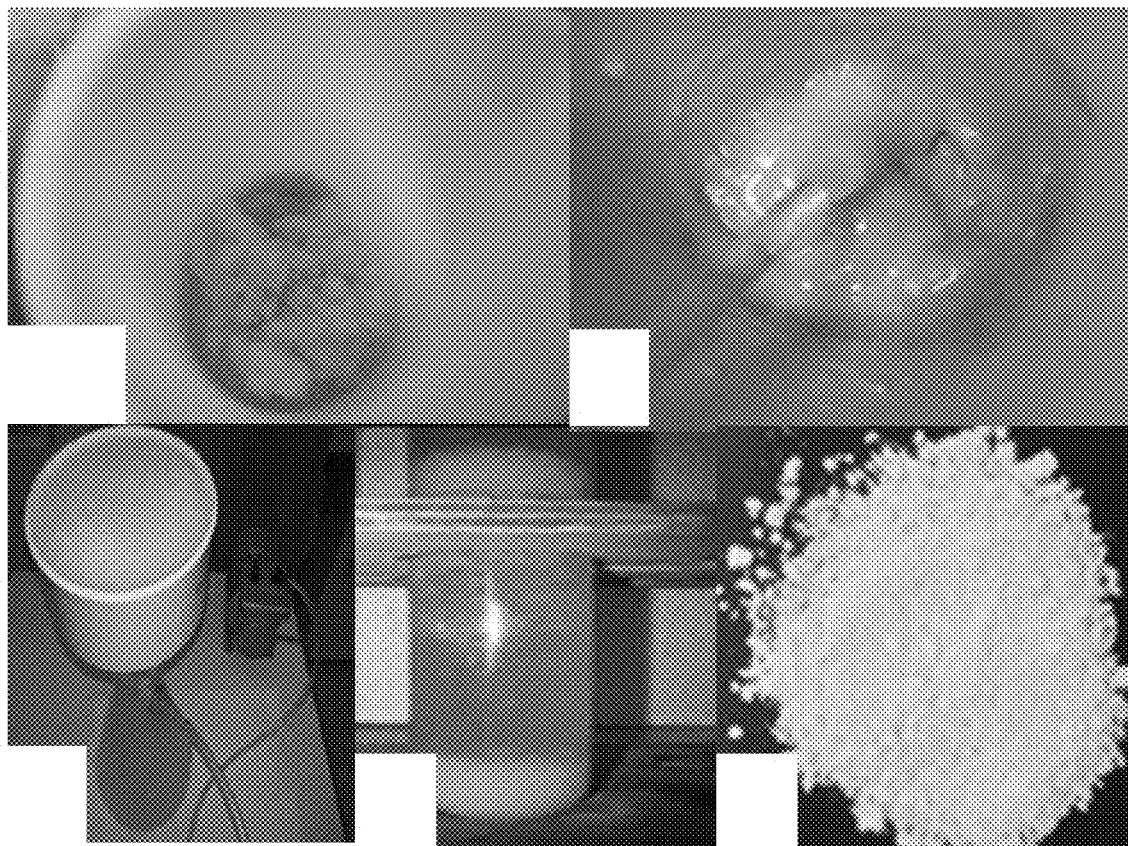

FIG. 3A
FIG. 3B
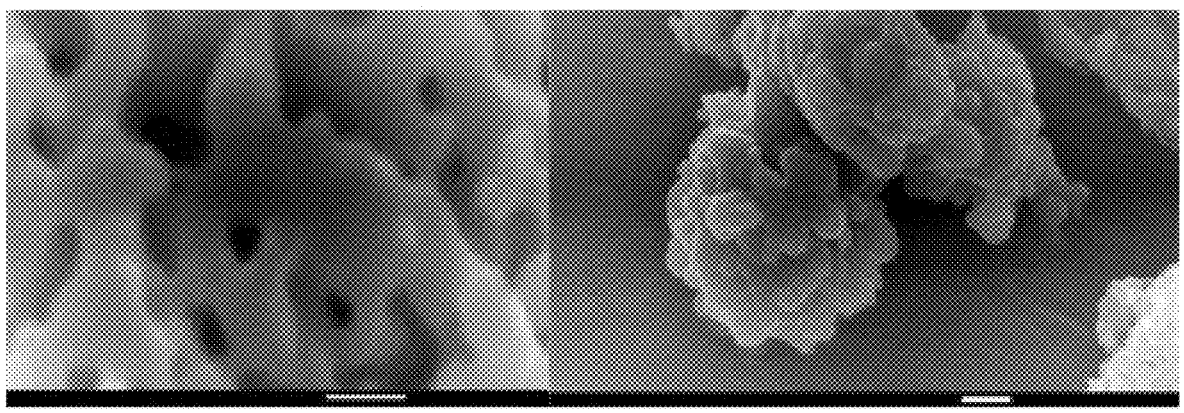
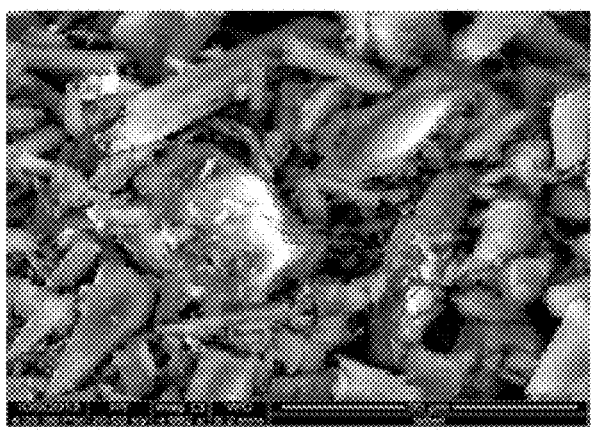
FIG. 3C
FIG. 3D

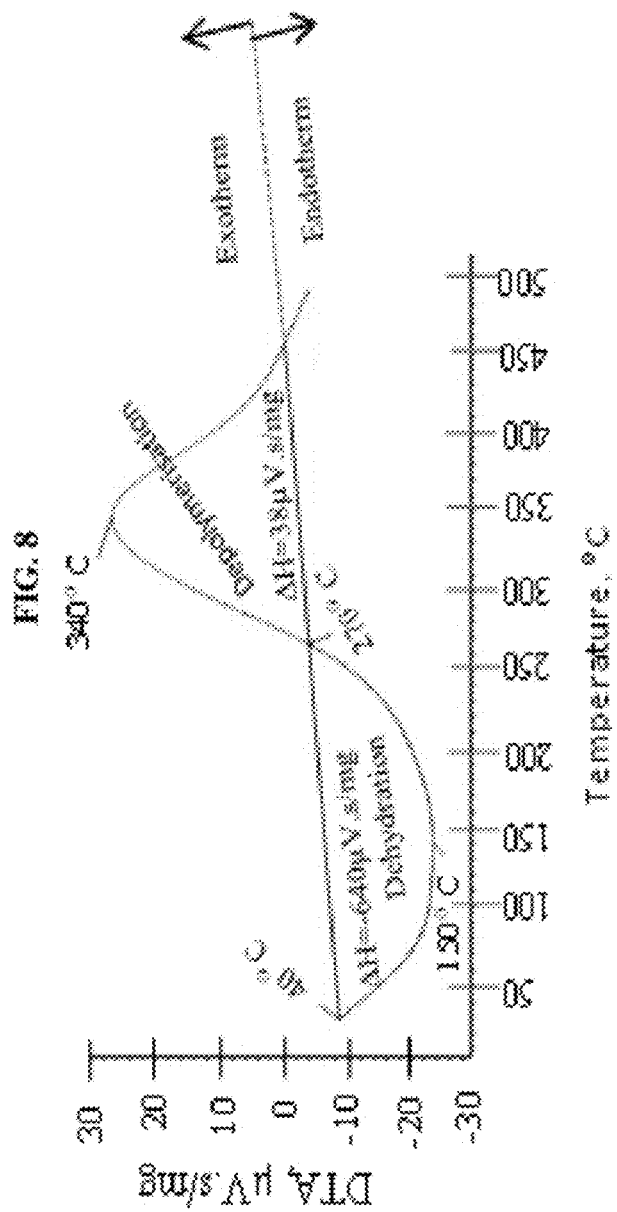

URCHIN-SHAPED NANOCRYSTALLINE MATERIAL

CROSS-REFERENCE TO RELATED APPLICATIONS

The present application is a Continuation of U.S. application Ser. No. 17/021,066, now allowed, having a filing date of Sep. 15, 2020, which is a Division of U.S. application Ser. No. 16/137,898, now U.S. Pat. No. 10,808,045 having a filing date of Sep. 21, 2018.

BACKGROUND

Field of the Invention

The invention pertains to wood technology and wood chemistry and to production of nanocrystalline cellulose.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Cellulose is the most abundant polymer on the Earth and is produced by members of the plant kingdom. It is composed of cellulose microfibrils which contain amorphous and crystallized regions. See Hindi, S. S. Z. 2017b. *Suitability of date palm leaflets for sulfated cellulose nanocrystals synthesis*. Nanoscience and Nanotechnology Research, 2017, Vol. 4, No. 1, 7-16. DOI:10.12691/nnr-4-1-2, incorporated herein by reference in its entirety.

Microcrystalline cellulose ("MCC") is produced by dissolving the amorphous regions of the cellulose microfibrils which liberates the crystalline regions and produces microcrystalline cellulose (MCC) or nanocrystalline cellulose (NCC). See Hindi, S. S. Z. 2017b, id.; Hindi, S. S. Z. 2017c. *Nanocrystalline Cellulose: Synthesis from Pruning Waste of Zizyphus spina christi and Characterization*. Nanoscience and Nanotechnology Research. 4(3):106-114. doi: 10.12691/nnr-4-3-4; and Hindi, S. S. Z. 2017d. *Microcrystalline cellulose: The inexhaustible treasure for pharmaceutical industry*. Nanoscience and Nanotechnology Research. 4 (1): 22-31; or Hindi, S. S., Albureikan, M. O., Al-Ghamdy, A. A., Alhummiany, H. and Ansari, M. S. 2017. *Synthesis and characterization of gum Arabic based bio plastic membranes*. Nanoscience and Nanotechnology Research, 4 (1): 32-42. DOI:10.12691/nnr-4-1-3; each incorporated herein by reference in its entirety. Alpha-cellulose is one of three classes of cellulose and has a high degree of polymerization and stability.

Conventionally, different processes such as reactive extrusion, enzyme mediated, steam explosion and acid hydrolysis, are used to produce MCC. Acid hydrolysis is favored and can be performed using mineral acids such as HCl, HBr, and $H_2SO_4$, or various ionic liquids. Usually 2.0-2.5 N HCl is used as the hydrolyzing agent for MCC production; Hindi, 2017d, id.

MCC is an important additive in the pharmaceutical, food, cosmetic, oil drilling, and plastic industries. In the pharmaceutical industry, it is an important tableting excipient due to its superior binding properties and ability to be directly compressed into tablets; Hindi, 2017d, id.

Like MCC, NCC can be synthesized via acid hydrolysis by using HCl, HBr or $H_2SO_4$. For example, treatment of α-cellulose with moderately concentrated sulfuric acid (64% w/w) for about two hours yields about 30 wt % NCC. The NCC produced has a short length ranging from 200-400 nm and a width less than 10 nm; Beck-Candanedo et al., 2005; Hindi. 2017; Araki, J., Wada, M., Kuga, S. Okano, T. *Low properties of microcrystalline cellulose suspension prepared by acid treatment of native cellulose*. Colloids Surf. A 1998, 142, 75-82; Beck-Candanedo, S., Roman, M., and Gray, D. G. 2005. *Effect of reaction conditions on the properties and behavior of wood cellulose nanocrystal*. Biomacromolecules. 6 (2):1048-54; and Hindi, S. S. Z. 2017b, each incorporated herein by reference in their entirety.

Hydrolysis with acids like HCl or HBr does not substantially affect the surface charge and sulfur content of the NCC. For example, acid hydrolysis using HCl produces NCC with minimum surface charge. However, it has been found that sulfuric acid provides more stable aqueous suspensions of NCC than hydrochloric acid (Araki et al., 1998, id.). Acid hydrolysis with $H_2SO_4$ leads to a negatively charged surface, due to the esterification of surface hydroxyl groups to give charged sulfate groups; see Dong, X. M., Revol, J. F., Gray, D. 1998. *Effect of microcrystalline preparation conditions on the formation of colloid crystals of cellulose*. Cellulose. 5: 19-32, and Beck-Candanedo et al., 2005, each incorporated herein by reference in their entirety.

In many conventional NCC production schemes, NCC is synthesized by acid hydrolysis of previously wetted α-cellulose precursor, such as wood pulp, using moderately concentrated $H_2SO_4$ (e.g., 64% wt/wt) and water ice for cooling. In one example of such a conventional process hydrolysis proceeds for about 60 minutes at a hydrolysis temperature between 45° and 70° C. After hydrolysis, the hydrolyzed precursor solution is quenched overnight by a large volume of distilled water—such as 10-times the volume of the hydrolysis solution—and then decanted. After that, it is centrifuged at 1,500 rpm and a solid, precipitated fraction containing fractured fibers is discarded. Subsequently, the collected supernatant solution is recentrifuged via five centrifugation cycles at 14,000 rpm to recover NCC which is then washed until neutralization. When the $H_2SO_4$ concentration is diluted to about 0.5 wt %, colloidal NCC appears.

To remove the $H_2SO_4$ residues from colloidal NCC, dialysis is performed with a concentration of 1 wt % NCC for about one week against deionized water. After that, ultrasonic treatment is applied at 0° C. for 30 minutes. Then, centrifugation is done at 14,000 rpm for about 45 minutes.

The resulting yield of NCC was found to range between 8-30%. See Habibi, Y., Lucia, L. A., and Rojas, O. J. 2010. *Cellulose Nanocrystals: Chemistry, Self-Assembly, and Applications*. Chem. Rev. 2010, 110, 3479-3500; Kumar, A., Negi, Y. S., Choudhary, V. and Bhardwaj, N. K. 2014. *Characterization of cellulose nanocrystals produced by acid-hydrolysis from sugarcane bagasse as agro-waste*. Journal of Materials Physics and Chemistry, 2 (1): 1-8. doi: 10.12691/jmpc-2-1-1; and Hindi, S. S. Z. 2017a. *Some Crystallographic Properties of Cellulose I as affected by cellulosic resource, smoothing and compution methods*, International Journal of Innovative Research in Science, Engineering and Technology (IJIRSET). 6 (1): 732-752. DOI:10.15680/IJIRSET.2017.061127; and Hindi, S. S. Z. 2017b, each incorporated herein by reference in their entirety.

Other processes using moderately concentrated sulfuric acid are known, such as that described by Ioelovich, ISRN Chem. Eng. Volume 2012 (2012), Article ID 428974, 7 pages at http://_dx.doi.org/10.5402/2012/428974, which describes a process using 50-65% sulfuric acid to treat MCC. However, only regenerated cellulose having a non-natural polymorph (cellulose II) was obtained by this process by using a concentration of 65% sulfuric acid.

Most global synthesis schemes for NCC use wood pulp as a cellulosic precursor and not MCC. Benefits of using microcrystalline cellulose (MCC) as a starting material instead of cellulosic fibers for synthesis of nanocrystalline cellulose (NCC), for example but not limited to the following items: (i) production of a NCC unity is attained while using less cellulosic precursor; (ii) the method consumes less concentrated $H_2SO_4$; (iii) MCC can be produced as a fine powder that is easy to handle within the synthesis apparatus rather than in a fibrous form of traditional cellulose; and MCC is more resistant to concentrated $H_2SO_4$ compared to α-cellulose, thus compared to cellulosic fiber the treatment of MCC with acid is less susceptible to degradation.

Other limitations of conventional NCC production processes include the requirement for use of expensive machinery, such as sonication baths, sonication props, centrifuges, dryers, lyophilizers and spray-driers or a complicated series of process steps such as requirements for centrifugation, sonication, neutralization, dialysis, and/or subsequent drying of an NCC product. Consequently, there is a need for a less complicated process that produces NCC in less time and at a lower cost.

In view of the limitations and drawbacks to conventional means for producing NCC, the inventors sought to develop and developed a simple, fast, convenient, industrially-scalable, and lower cost way of manufacturing NCC.

BRIEF SUMMARY OF THE INVENTION

One non-limiting aspect of the invention is method for producing nanocrystalline cellulose ("NCC") from a precursor that contains microcrystalline cellulose ("MCC") by fragmenting MCC and liberating nanocrystalline cellulose. Hydrolytic fragmentation of MCC occurs in the presence of frozen concentrated sulfuric acid (98.06%) which form a paste in combination with the MCC substrate. Flash hydrolysis is carried out in a narrow low temperature range for a short period of time by sudden dilution of the paste with a mixture of cold water and hair-shaped ice forming a turbid solution. NCC is recovered from the turbid solution, washed and neutralized, and optionally dried. It is not necessary to use equipment such as a centrifuge to recover the NCC as it may be simply recovered using inexpensive filter paper or a Gooch crucible.

These and other features of the invention will become readily apparent upon further review of the following specification and drawings.

BRIEF DESCRIPTION OF THE DRAWINGS

FIG. 1A describes the production of nanocrystalline cellulose from microcrystalline cellulose by icy $H_2SO_4$-hydrolysis.

FIG. 1B is a photo of crude paste containing NCC formed by treatment of MCC with concentration sulfuring acid.

FIG. 1C depicts a vacuum filtration system with continuous cooling.

FIG. 1D shows precipitated NCC ready to be filtered using Whatman paper no. 44.

FIG. 1E shows oven-dried NCC powder produced from the filtrate.

FIG. 3A shows a SEM micrographic image of the NCC backbone of NCC (35,000×).

FIG. 3B depicts flower shaped aggregates of NCC (10,000×).

FIG. 3C. shows a SEM micrograph of rod-shaped NCC.

FIG. 3D depicts a SEM micrograph of a stratified agglomeration of NCC.

FIG. 8. Shows a differential thermal analysis (DTA) of NCC synthesized as disclosed herein.

DETAILED DESCRIPTION OF THE INVENTION

Figure 2A:
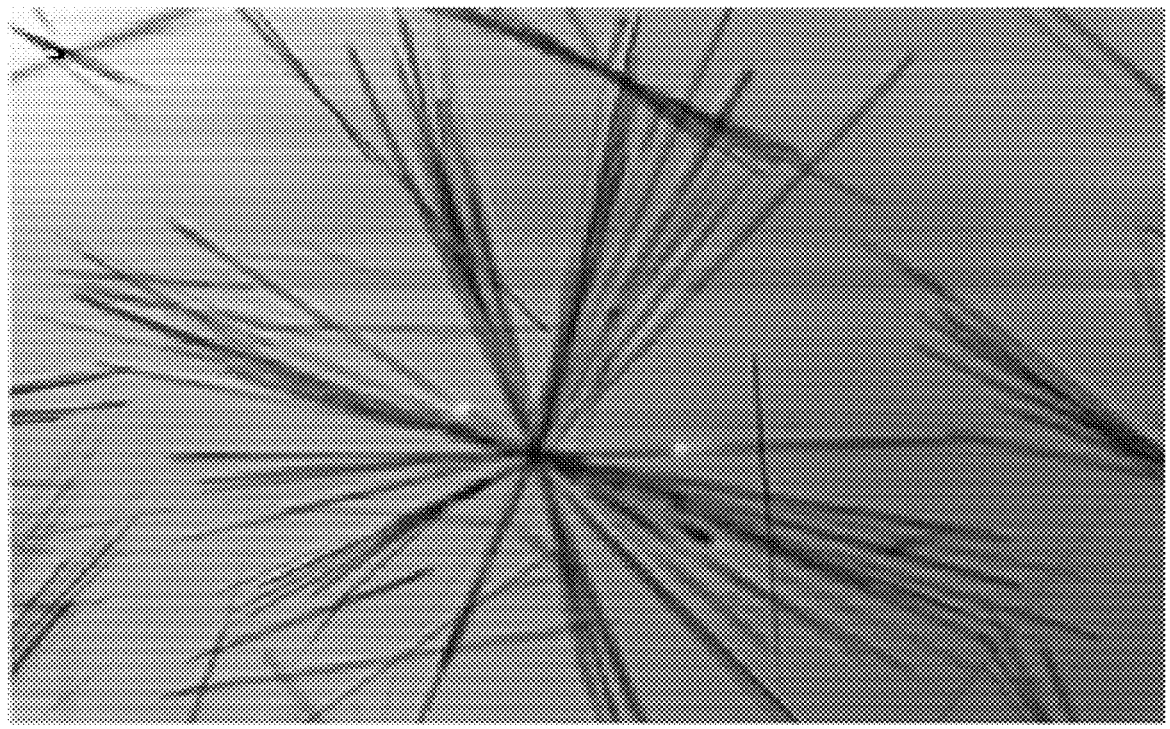
FIG. 2A shows an optical image of urchin shaped NCC produced as a final crystal growth architecture.

The invention employs MCC as a starting material or substrate for NCC production. The inventors have found that this confers several benefits compared methods that use other cellulosic substrates. These benefits include production of NCC unity using less cellulosic precursor, consumption of less sulfuric acid, a reduced risk of MCC substrate degradation by acid compared to other cellulosic substrates, and easier handling, standardization, and machine processing of a MCC cellulosic substrate in apparatus used to hydrolyze and recover a NCC product.

Microcrystalline cellulose or MCC is composed of glucose units connected by 1-4 beta glycosidic bonds. These linear cellulose chains are bundled together as microfibrils spiraled together in the walls of plant cells. Each microfibril can exhibit a high degree of three-dimensional internal bonding resulting in a crystalline structure that is insoluble in water and resistant to reagents. There are, however, relatively weak segments of the microfibril with weaker internal bonding. These are called amorphous regions because of the single-phase structure of microfibrils. The crystalline region is isolated to produce microcrystalline cellulose. The MCC can be synthesized by different processes such as reactive extrusion, enzyme mediated, steam explosion and acid hydrolysis. The later process can be done using mineral acids such as HCl, HBr or $H_2SO_4$ as well as ionic liquids. The role of these reagents is to destroy the amorphous regions and retain the crystalline domains. The degree of polymerization of MCC is typically less than 400, such as 125, 150, 175, 200, 250, 300, 350, <400 or 400 (or any intermediate value within this range). MCC and NCC may include those containing or obtained from chemically modified celluloses, such as cellulose containing sulfate groups.

Alpha-cellulose is one of three classes of cellulose and has a high degree of polymerization and stability. Alpha cellulose has both alternated regions, namely crystalline and amorphous regions extended along with microfibril axe; see Hindi, S. S. Z. 2017a. *Microcrystalline cellulose: The inexhaustible treasure for pharmaceutical industry*. Nanoscience and Nanotechnology Research. 4 (1): 22-31. 10.12691/nnr-4-1-3; Hindi, S. S. Z. 2017b. *Differentiation and Synonyms Standardization of Amorphous and Crystalline Cellulosic Products*. Nanoscience and Nanotechnology Research. 2017; 4(3):73-85. doi: 10.12691/nnr-4-3-1; Hindi, S. S. Z. 2017$^c$. *Some Promising Hardwoods for Cellulose Production: I. Chemical and Anatomical Features*. Nanoscience and Nanotechnology Research. 2017; 4(3):86-97. doi: 10.12691/nnr-4-3-2; Hindi, S. S. Z. 2017$^d$. *Suitability of date palm leaflets for sulphated cellulose nanocrystals synthesis*. Nanoscience and Nanotechnology Research, 2017, Vol. 4, No. 1, 7-16. DOI: 10.12691/nnr-4-1-2; Hindi, S. S. Z. 2017$^e$. *Nanocrystalline Cellulose: Synthesis from Pruning Waste of Zizyphus spina christi and Characterization*. Nanoscience and Nanotechnology Research. 2017; 4(3):106-114. doi: 10.12691/nnr-4-3-4; and Hindi, S. S. Z. 2017$^f$. *Some Crystallographic Properties of Cellulose I as Affected by Cellulosic Resource, Smoothing, and Computation Methods*. International Journal of Innovative Research in Science, Engineering and Technology (IJIRSET). 6 (1): 732-752. DOI:10.15680/IJIRSET.2017.061127.

MCC substantially contains only the crystalline regions of the cellulosic microfibrils; see Hindi, S. S. Z. and Abohassan, R. A. 2016. *Cellulosic microfibril and its embedding matrix within plant cell wall*. International Journal of Innovative Research in Science, Engineering and Technology 5 (3): 2727-2734; Hindi, S. S. Z. 2016$^a$. *The interconvertiblity of cellulose's allomorphs*. International Journal of Innovative Research in Science, Engineering and Technology (IJIRSET). 6 (1): 715-722. DOI:10.15680/IJIRSET.2017.0601125. Hindi, S. S. Z. 2016b. *Birefringence of bio-based liquid crystals*. International Journal of Innovative Research in Science, Engineering and Technology (IJIRSET). 6 (1): 708-714. DOI:10.15680/IJIRSET.2017.0601124. As appreciated by the inventors, MCC is a homogenous precursor for synthesis of NCC because it excludes amorphous regions due to its previous acid hydrolysis from an α-cellulose precursor. Other non-MCC precursors or special forms of cellulose such as linter, starch, freeze-dried cellulose, lyophilized cellulose, hemicellulose, unrefined alpha-celluloses or ground cellulosic fibers are not required.

Nanocrystalline cellulose or NCC describes cellulose particles, regions, or crystals that contain nanometer-sized domains. Dimensions of NCC depend on the nature of the MCC precursor material, hydrolysis time, hydrolysis, temperature and on handling, such as on washing, filtration and drying conditions.

In some embodiments, the nanocrystalline cellulose material is characterized by an average length-to-width aspect ratio of particles from about 10 to about 1,000, such as about 15, 20, 25, 35, 50, 75, 100, 150, 200, 250, 300, 400, or 500 (or any intermediate value within these ranges).

Nanofibrils are generally associated with higher aspect ratios than nanocrystals. Cellulose nanocrystals are typically rigid rod-shaped monocrystalline cellulose domain (whisker) with 1, 5, 10, 20, 50, to 100 nm (or any intermediate value within this range) in diameter and tens to hundreds, such as 10, 20, 50, 100, 200, 300, 400, 500, 600, 700, 800, 900, 1,000 or >1,000 nanometers in length. Aspect ratios for nanocrystals are determined by dividing their lengths by their diameters. For example, nanocrystals having respective lengths of 100, 200, 300, 400, or 500 nm and diameters of 4 nm have aspect ratios of 25 to 125.

Nanofibrils may have a length of about 2,000 nm and diameter range of 5 to 50 nm, translating to an aspect ratio of 40 to 400. In some embodiments, the aspect ratio is less than 50, less than 45, less than 40, less than 35, less than 30, less than 25, less than 20, less than 15, or less than 10.

The crystallinity index (CI) of the NCC made by the method of the invention may range between 40, 50, 60, 70, 80, 90, 95, 96, 97, 98, 99, 99.5, <100, or 100% (or any intermediate value within this range). Preferably, the CI of the NCC at least 85. The NCC made by the invention may exhibit an average crystallite size between about 1.8, 2.8, 3.8, or <5.0 or any intermediate value within this range. Lattice spacing in the NCC of the invention may fall within the range 0.19, 0.20, 0.21, 0.214, 0.22, 0.23, 0.24, 0.25, or any intermediate value within this range.

Surprisingly, the inventors found that the method of the invention can fragment the MCC precursor into NCC that has normal nanometric properties similar to those of cellulose I which is a form of cellulose exhibiting hydrogen-bonding found in natural cellulose. These fragments of MCC differ from regenerated cellulose II or chemically-treated forms of cellulose such as cellulose III or cellulose IV. In another embodiment the flash hydrolysis of the invention was found to graft three sulfate groups onto the available carbon site numbers 3, 4, and 6 of the glucopyranose unit constituting the cellulose chain.

Hydrolysis is cleavage of chemical bonds by the addition of water. Hydrolysis of amorphous regions of the MCC starting material is conducted under cooling conditions, such as at a temperature of 25, 20, 15, 10, 5, or 0° C., preferably, hydrolysis occurs rapidly upon dilution of a paste of concentrated sulfuric acid and MCC in a large volume of water and water ice crystals at a temperature within the range of 10–15° C. The mixture of MCC and concentrated sulfuric acid may be cooled using a mixing and/or hydrolysis container or chamber that is equipped with a jacket holding liquid nitrogen and with a hollow stirrer filled with liquid nitrogen.

Dilution after contact and hydrolysis of the MCC starting material by concentrated sulfuric acid under cooling conditions, of the hydrolyzed MCC (usually in the form of a paste) is carried out, preferably, very rapidly, with water or with an aqueous buffer. Dilution may be performed under cooling conditions and/or under an inert or reduced oxygen atmosphere to inhibit oxidation of NCC. It is not necessary to use other liquids, such as ethanol or other alcohols, ethers, or liquid gases such as liquid nitrogen, to make the paste or as components of a hydrolysis mixture. It is not necessary to cool the substrate, paste or hydrolysis mixture using liquid gases like liquid nitrogen or cooled gas vapors.

Filtration includes various ways of separating materials by filtration such as those known in the art. A filter paper or other filter or filtration device having a pore size in the range of 0.4, 0.5, 1, 1.5, 2, 2.5, 3, ≥4 μm may be selected to recover the NCC. Different grades of filter paper may be selected depending on the size of the NCC particles to be recovered, for example, Grade 602h filter paper has a pore size of 2 μm and in a preferred embodiment, Whatman filter paper #44 type filter paper (or its equivalent), which has a pore size of 3 μm, is used to recover NCC.

Gooch crucibles and fritted glass filters may also be used to recover the NCC, for example, a Gooch crucible may be fitted with a fritted glass filter having a fine pore size in the range of 0.4, 0.5, 1.0, 1.5, 2, 2.5, 3, 3.5, and ≥4 µm and used to recover the NCC. Other modes of filtration are known and may be adapted to recover the NCC produced by the method of the invention. These include filtration methods using surface filters which trap NCC particles. Devices such as a Buchner funnel, vacuum filter, rotary vacuum-drum filter, belt filter, or a cross-flow filter, or screen filters, may be adapted to recover NCC. Centrifugation, dialysis, lyophilization, freeze-drying, or further chemical treatments may be performed in some embodiments but are not required.

Non-limited embodiments include the following.

A method for making nanocrystalline cellulose ("NCC") including contacting frozen concentrated sulfuric acid with microcrystalline cellulose ("MCC") at a temperature ranging from about 10° C. to about 15° C. for a time sufficient to form a cellulosic paste containing hydrolyzed MCC, diluting the paste containing hydrolyzed MCC in a mixture comprising liquid water and water ice to precipitate NCC, and separating the precipitated NCC from other components in the mixture such as water, sulfuric acid, or MCC, thus making NCC.

Flash hydrolysis is fast and hydrolysis may take no more than 1, 2, 3, 4, 5, 6, 7, 8, 9, 10 mins after which time it may be terminated by neutralization, acid separation, filtration, dilution, or washing. In some embodiments, this method will include each of following steps: preparation of MCC before hydrolysis, flash hydrolysis, neutralization, filtration, drying, and grinding.

Unlike prior methods the inventors use concentrated sulfuric acid most preferably concentrated to 98.06% wt/wt. Conventional methods avoid using a high concentration of sulfuric acid to protect cellulosic precursors from the exothermic effects of exposure to highly concentrated acids including highly oxidative conditions and the high exothermic heat release that can quickly carbonize a cellulosic precursor.

In contrast, the invention ameliorates or avoids the negative effects of using a high concentration of sulfuric acid and uses an efficient cooling process to compensate for the heat arising from the hydration of the cellulose caused by the acid as well as a short hydrolysis time.

Unlike conventional hydrolysis processes the invention carefully controls or compensates for the amount of heat generated by dilution of the concentrated sulfuric acid, replacement of hydroxyl groups on MCC and generation of water molecules from hydroxyl ions released from the MCC and the hydrogen ions of the $H_2SO_4$. Cellulose hydrolysis is attained within a temperature range of −30° C. to 10° C., for example, at −30, −25, −20, −15, −10, −5, 0, 5, 10, 15, 20, 25, or 30° C. or any intermediate value or subrange within this range; preferably between about 10° C. to 15° C., most preferably about 15° C. The temperature of frozen sulfuric acid or water ice may be selected to attain or maintain this temperature range. For example, frozen sulfuric acid may have a temperature ranging from <−40, −40, −30, −25, −20, −15, −10, −5, 0 or +3° C. One preferred cooling process includes two parallel routes: using frozen $H_2SO_4$ and using hair-shaped ice.

The quantity, temperature, and shape of the water ice is selected to maintain a hydrolysis temperature within the desired range, for example, from 10, 11, 12, 13, 14, 15, 16, 17, 18, 19, or 20° C. Ice will generally have lower temperature than the desired hydrolysis temperature to permit removal of excess heat, for example, water ice may have a temperature ranging from <−40, −40, −35, −30, −25, −20, −15, −10, −5, or 0° C. which allows it to absorb exothermic and excess heat generated by flash hydrolysis conducted at a higher temperature of 10 to 20° C.

The water ice may be in the shape of granules, scales, or in an elongated form, such as a in a hair shape. In some embodiments ice is used that has an average diameter (granules), thickness (scales) or length and diameter (elongated) in the range 1, 2, 3, 4, 5, 6, 7, 8, 9, 10 mm. Hair-shaped ice may be made by a variety of different methods including that exemplified herein. It may have a ratio of diameter to length of about 1, 2, 3, 4, 5, 6, 7, 8, 9, 10, 20, 30, 40, 50, 100, 200, 300, 400, 500 or 1,000; and a diameter of 0.01, 0.02, 0.05, 0.1, 0.2, 0.1, 0.5, 1.0, 1.2, 1.5 or 2.0 mm as well as any intermediate value within these subranges. In a preferred embodiment, the hair-shaped ice will have a diameter of about 1 mm and a length of about 3 mm. Hair-shaped ice is advantageously used for cooling due to its ability to provide rapid cooling commensurate with heat release caused by flash hydrolysis. Hair-shaped ice may be made by a variety of different methods including that described in the Example below.

Hair-shaped ice may be used for cooling either for the cellulosic precursor, for sulfuric acid, during hydrolysis, or for a hydrolyzed mixture during or after each process step, including during neutralization, washing or filtration. Cooling or supercoiling prevents or reduces degradation of the MCC substrate, the NCC product as well as equipment used to process r the substrate MCC into NCC and recover the NCC. For example, cooling prevents discoloration of a paste of MCC substrate and sulfuric acid into a brown paste containing oxidized or degraded cellulose.

In some embodiments of the invention, the MCC precursor is in the form of precooled cellulosic fibers at a temperature of no more than 0, 5, 10, 11, 12, 13, 14, 15, 16, 17, 18, 19, 20, 21, 22, 23, 24, or 25° C. The MCC precursor may be dry or prewet.

In other embodiments, the frozen sulfuric acid has a concentration of at least 50, 60, 70, 80, 90, 91, 92, 93, 94, 95, 96, 97, 98 or >98 mass %. Preferably, the sulfuric acid has a concentration of about 98.06 mass %. Advantageously commercially available concentrated sulfuric acid, such as sulfuric acid having a concentration of about 98.06 mass % is used. Preferably, sulfuric acid having concentrations of up to 10, 20, 30, 40, 50, 60, 70, 80, 90, 95, or <98% are not used.

In some embodiments of the invention, hydrolysis occurs at a temperature ranging from 0, 1, 2, 3, 4, 5, 6, 7, 8, 9, 10, 11, 12, 13, 14, 15, 16, 17, 18, 19, 20, 21, 22, 23, 24, or 25° C., preferably from about 10° C. to 15° C., more preferably at about 15° C.

In some embodiments, frozen concentrated sulfuric acid and MCC precursor is contacted to form a paste at a wt/wt ratio of frozen concentrated sulfuric acid to MCC of 4:1 to 1:4, 3:1 to 1:3, 2:1 to 1:2, 1.5:1 to 1:1.5, or any intermediate ratio value. Preferably, the contacting occurs at a ratio about 1.25:1 to 1:1.25, more preferably at a ratio about 1:1.

In some embodiments of the method described above, the diluting occurs at a ratio of $H_2O$ to MCC of 4:1 to 1:4, 3:1 to 1:3, 2:1 to 1:2, 1.5:1 to 1:1.5 (wt/wt), or any intermediate ratio value; preferably at a ratio ranging from 2:1 to 1:2 (wt/wt). Preferably distilled water is used for diluting, though in some embodiments the water may contain buffers, salts or other solutes, for example a component that facilitates NCC recovery or neutralization, or other solutes that do not substantially interfere with recovery of NCC.

In other embodiments, separating NCC from a hydrolyzed mixture is performed by filtering the hydrolyzed MCC to recover NCC; is performed by filtering the hydrolyzed MCC to recover NCC and wherein the filtering is performed at a temperature ranging from 0, 5, 10, 15, 20 to 25° C. (or any intermediate value within this range). In some embodiments the filtering is performed at a temperature ranging from 0° C. to 15° C., such as at 0, 1, 2, 3, 4, 5, 6, 7, 8, 9, 10, 11, 12, 13, 14 or 15° C.

In other embodiments, the method described herein further includes washing the recovered NCC with water or a buffer to increase the pH of the NCC. In some embodiments other organic solvents such as ethanol, methanol or aqueous-organic mixtures thereof may be used to wash the NCC. In other embodiments an aqueous solution containing one or more salts or buffers may be used to wash the NCC; or may further include washing the recovered NCC with water to increase the pH of the NCC to at least pH 5.5 to pH 8.5 or any intermediate value within this range such as pH 5.5, 6.0, 6.5, 6.75, 7.0, 7.25, 7.5, 8.0 or 8.5. In some embodiments, the recovered NCC is washed with water to increase the pH of the NCC to at least pH 6.5 to pH 7.5 and then further dried after washing.

In some embodiments, the MCC is contacted directly with the concentrated sulfuric acid to form a paste. In other embodiments, the MCC substrate may be prewet or combined with water that participates in hydrolysis.

In some embodiments, one or more steps of the method may be performed under conditions than minimize contact of NCC with oxygen, for example, under an inert atmosphere or atmosphere having 0, 1, 2, 5, 10, 15, 16, 17, 18, 19, 20 to <21% (or any intermediate value within this range) oxygen or substantially no oxygen at all. Oxidation of NCC may also be inhibited by the addition of an antioxidant.

The method of the invention may produce no more than 10, 20, 30, 40, 50, 60, 70, 80, or 90 minutes a yield of NCC of at least about 30, 35, 40, 45, 50, 60, 65 wt % based on the weight of the MCC. Advantageously the duration of the contacting, diluting and separating steps in aggregate do not exceed a batch duration of 15 minutes and yield at least 30, 40, 50 or 60 wt % NCC. Here, the batch duration is the time consumed from the time when concentrated sulfuric acid is contacted with MCC up to the time of obtaining a weight unity of cellulose nanocrystals.

Another embodiment of the invention is directed to a composition comprising MCC, frozen concentrated sulfuric acid, and water ice crystals, such as hair-ice crystals. Such a composition may have a ratio of MCC precursor to concentration sulfuric acid, or ratio of MCC precursor to water or water ice as disclosed above.

Other embodiments of the invention include the NCC produced by the method disclosed herein. The NCC produced may have an average degree of polymerization from about 100, 200, 300, 400, 500, 1,000, to about 1,500 or any intermediate degree of polymerization within this range and/or be substantially composed of cellulose I. The NCC may be in a form of nanocrystalline cellulose or nanofiberous cellulose. In some embodiments, the NCC produced by the method of the invention may be in the form of "furry" nanocrystal urchins. These may range in furriness (radius/urchin) between 150, 200, 300, 320, 350, 400, 450, 500, 600 or more and have a mean width ranging from 90, 100, 110, 120, 130, 140, 150, 160, 170, 180, 190, 200, 250, or >250 µm. Other physical features of NCC produced according to the invention using hair-ice cold hydrolysis may include a crystallinity index (%) ranging from about 2.25, 2.3, 2.35, 2.4, 2.42, 2.5, 2.55, 2.6, to 2.65; a crystallite size ranging from about 2.25, 2.3, 2.35, 2.4, 2.42, 2.45, 2.5, 2.55, 2.6, 2.65, to 2.7 nm; and/or a lattice spacing 0.265, 0.270, 0.273, 0.275, or 0.28 nm. The NCC produced according to the invention as disclosed herein preferably has a negligible amorphous cellulose content, such as less than 5, 4, 3, 2, 1, 0.5, or 0.1 wt %.

The NCC produced by the method discloses herein may be used in one or more of the following ways.

Foods and Pharmaceuticals. NCC can be used as a tableting or other pharmaceutical excipient. It can also be used as a low calorie replacement for carbohydrate additives used as thickeners, flavor carriers and suspension stabilizers in a variety of food products and are useful for producing fillings, crushes, chips, wafers, soups, gravies, puddings and other food products.

Adhesives. The NCC produced by the method of the invention can be used to enhance the wet and dry strengths of an adhesive. Through rheology modification, enhanced bond-forming and inherently high strength, NCC can be used to boost performance in wood adhesives such as phenol-formaldehyde and urea/melamine-formaldehyde. NCC may be added to polymeric plastics as a filler or backbone structural material to increase their strength up to 10, 20, 50, 100, 200, 500, 1,000, or 2,000 times.

Paper and non-woven. When used in conjunction with traditional materials in paper production, the NCC produced by the method of the invention can improve product quality. When integrated into super absorbent materials the NCC increases absorption and improves structural integrity or paper or paperboard products as well as adsorbent materials. Hygiene products such as cosmetic or medical wipes, wound dressings, diapers, incontinence products, sanitary napkins, tampons and other absorbent materials may incorporate NCC. NCC may also be used as a barrier material in paper and paperboard products, for example, to provide grease or oil-resistance or to enhance retention, dry strength, or wet strength of the paper or nonwoven product. Nanocrystalline cellulose can be used to prepare flexible and optically transparent paper. Such paper is an attractive substrate for electronic devices because it is recyclable, compatible with biological materials and after use and disposal easily degrades.

The oil and gas industry. NCC may be incorporated into a variety of oil-field fluids and materials such as fracturing fluids, drilling muds and pumping, pressure fluids, as well completion fluids.

Another embodiment of the invention is an apparatus that includes at least one container suitable for hydrolysis of MCC in the presence of frozen sulfuric acid or sulfuric acid and water, at least one stirrer, and at least one separator; wherein the container comprises a cooling jacket that can be filled with liquid nitrogen, the stirrer is hollow and can be filled with liquid nitrogen, the stirrer is positioned inside the container, and the separator is operatively connected to the container so that it can receive and separate or recover a precipitate of NCC. These parts may be made of stainless steel or another material resistant to degradation by sulfuric acid, such as a thermally conductive polymer.

In some embodiments separate containers will be used to mix concentrated sulfuric acid and MCC and to perform hydrolysis by addition or dilution with water. These containers may be operatively attached so that a paste of MCC and concentrated sulfuric acid can be pumped, sprayed, injected, or otherwise transferred from a first mixing container to a second hydrolysis container which contains water or water ice or to which water or water ice is added to flash dilute the paste of sulfuric acid and MCC. The second container for receiving the paste may be equipped with a stirrer or other mixing apparatus such as a radial impeller to create a radial flow perpendicular to ingredients to be mixed when introduced as a vertical flow; or a pitch impeller that creates an axial flow perpendicular to ingredients to be mixed when introduced as a horizontal flow into the second container. Preferably stirrers or other mixing apparatuses are refrigerated, for example, by an internal space or circulation device for internal cooling with liquid nitrogen.

In other embodiments a single container will be used to mix the sulfuric acid and MCC and to contact it or otherwise dilute it with water or water ice.

The first and/or second containers may be equipped with stirrers or one or more mixing apparatus such as those described above as well as inlets for substrate materials, outlets for mixed product, such as outlets operably attached to a downstream separation or filtration device, or pH, temperature, viscosity or rheological sensors, meters, valves or controllers. Temperature controllers may detect and adjust the temperature of the MCC being hydrolyzed or of NCC-containing product after hydrolysis. A container or containers used to mix the concentrated sulfuric acid and MCC and for hydrolysis may further be operatively attached to one or more filters and the filters may be operative attached to one or more driers. In embodiments with separate mixing and hydrolysis containers, one or both of the containers may be equipped with a cooling jacket and hollow stirrer as described above and controllers may also be employed to adjust the temperature or flow of liquid nitrogen to a cooling jacket or stirrer so as to maintain a desired hydrolysis temperature in the hydrolysis container.

This apparatus may be further operatively connected to an oven or other drier and/or may include at least one separator that is a filter, such as paper or filter paper.

The apparatus may also comprise a grinder, such as an impact, rotary, or ball mill grinder to grind the MCC substrate or dried NCC. In other embodiments, the MCC or NCC may undergo homogenization or microfluidization.

The apparatus may also include a thermostat and/or controller to regulate the mixing ratio of concentrated sulfuric acid to MCC, to regulate the amount of water used to dilute a paste of concentrated sulfuric acid and MCC, or to regulate the mixing time or temperature of the concentrated sulfuric acid and MCC or regulate the diluting temperature or amount of time between dilution of the paste and separation of the NCC.

In some embodiments, NCC is produced and recovered without sonication, ultrasonic processing, and/or without centrifugation.

EXAMPLES

The following examples illustrate various aspects of the present invention. These examples are not to be construed to limit the claims in any manner whatsoever. As apparent from the examples, the invention provides an easy and convenient cooling method to remove excessive heat generated by contacting MCC with concentrated sulfuric acid may otherwise degrade or deform or reduce the yield of the resulting crystalline NCC product, for instance, by excess heat or oxidation and by converting Cellulose I structure into a Cellulose II structure. Moreover, fine residues of such thermal or oxidative processes can form and cause other technical problems in the subsequent recovery or purification of NCC, especially during filtration.

As shown below, the invention solves these problems by maintaining the MCC and NCC under conditions with minimize or eliminate decomposition, for example, by providing continuous cooling for the MCC precursor as well a temperature within a narrow thermal range during hydrolysis, or hydrolysis and filtration, or by use of an inert or reduced oxygen atmosphere.

In a preferred embodiment, cooling using frozen sulfuric acid in combination with fine water ice granules provides a superior MCC hydrolysis process because it provides sufficient time for mixing the acid with the MCC precursor before substantial thermal deterioration of the MCC precursor by the exothermic heat released by the hydration effect of the concentrated $H_2SO_4$ on the MCC-precursor.

The method of the invention can be performed without requiring complex techniques and devices that are applied for the ordinary schemes of production of NCC which require sonication or centrifugation. The method of the invention is easily scalable and can be used to produce large quantities of high quality NCC required globally while reducing production time and cost.

Example 1

Production of NCC from MCC Using Concentrated Sulfuric Acid

Raw Materials Precursors for microcrystalline cellulose ("MCC"). Alpha-cellulose isolated from *Zyziphus spina* var. Christi was used as a cellulosic precursor of MCC production. The MCC was conventionally synthesized using 2N HCl at 80° C. for three hours. This hydrolyzing agent was used to dissolve the amorphous region within the cellulosic microfibrils.

Raw materials precursors for nanocrystalline cellulose. Microcrystalline cellulose or MCC was used as the precursor for NCC production.

The hydrolysis process for synthesizing NCC. Concentrated sulfuric acid (98.06%), deionized water, fine water ice granules (FWIG) were used for hydrolysis.

Hydrolysis of the MCC to produce NCC. Frozen pure concentrated sulfuric acid (98.06%) was mixed with the precooled MCC at an acid/cellulose ratio of 1:1 (wt/wt) to form a bright white paste, see FIG. 1B. The paste was suddenly diluted in a mixture of cold water and fine water ice granules at a water/cellulose ratio of 1:1 (wt/wt) to form a turbid solution which was then filtered under cooling. The filtered NCC precipitate was washed with cold water until neutralization to pH 7 and then dried to yield NCC.

Characterization of Cellulose Nanocrystals. The properties of the NCC studied were crystallinity index (CI), crystallite size (CS) and lattice spacing (LS) by XRD, functional groups by Fourier transform infrared (FTIR), mass loss by thermogravimetric analysis (TGA) and the energy released and absorbed by differential thermal analysis (DTA).

Sample Preparation for the Different Properties Determinations. The NCC samples specified for XRD, FTIR and TGA were ground in a ball mill to passes through a 100 mesh and retained on a 120 mesh. For the NCC samples chosen for SEM and TEM spectroscopies, NCC solutions were dispersed into absolute ethanol at a concentration of 1% wt/wt and sonicated for an hour. A clear droplet was mounted onto an Al-stub for SEM or onto a copper grid for TEM tests.

The Optical Vision System. The optical speculation unit used to study the NCC samples consists of a light microscope (CE-MC200A) with a magnification power of 10× with suitable vision system (OPTIKA PRO 5 Digital Camera-4083.12). Vision PRO 4 software was used to pick up and process images.

Scanning Electron Microscopy (SEM). SEM spectroscopy was used to investigate the surficial morphology as well as anatomical features of the NCC. The samples were placed onto double side-carbon tape on Al-stub and air-dried. All samples were sputtered, before examination, with about 15 nm thick gold layer (JEOL JFC-1600 Auto Fine Coater) in a vacuum chamber (Tang et al., 1997). The NCC samples were tested using a SEM Quanta FEG 450, FEI, Amsterdam, Netherlands. The microscope was operated at an accelerating voltage which varied from 5-20 kV.

Transmission Electron Microscopy (TEM). TEM spectroscopy of the NCC samples was done to visualize their component building blocks leading to the final architecture formed via their crystal growth. Phosphotungstic acid was used to dye the NCC samples. The NCC was examined by TEM (JEM-1011 JEOL, Japan) at an operated voltage of 100 kV.

The X-Ray Diffraction (XRD). The XRD spectra of the NCCs were studied to determine their crystallinity using the XRD-D2 Phaser Bruker (USA). The generator was operated at 30 KV and 30 mA for a period of 50 minutes using CuKa radiation with a wavelength of 0.15418 nm. The tests were done in the reflection mode at a scan speed of 4°/min in steps of 0.05°. All samples were scanned between 2θ=4° to 30°, see Hindi, 2017a, id.

The Crystallinity Index (CI). First, individual crystalline peaks were isolated using the curve-fitting process from the diffraction intensity profiles as described by Park et al., 2010, id.; Garvey, C. J., Parker, I. H., and Simon, G. P. 2005. *On the interpretation of X-ray diffraction powder patterns in terms of the nanostructure of cellulose I fibres*, Macromolecular Chemistry and Physics. 206 (15): 1568-1575, 2005. DOI: 10.1002/macp.200500008; and Hult, E. L., Iversen, T., and Sugiyama, J. 2003. *Characterization of the supenmolecular structure of cellulose in wood pulp fibers*. Cellulose. 10 (2): 103-110, 2003, each incorporated herein by reference in their entirety.

The CI was calculated by dividing the diffractogram area of crystalline peaks on the total area of the whole diffractogram. The area under the whole curve was estimated by summing of adjacent trapezoids using Excel (Microsoft, USA) as indicated by Hindi (2017$^a$), id.

The Crystallite Size (CS). The CS (nm) of the NCC backbone was calculated by Scherrer equation with respect to the crystallographic plane, namely 002 as follow: $CS=K\lambda/\beta_{1/2} \cos\theta$, where K is the correction factor and normally is considered to be 0.91, $\lambda$ is the radiation wavelength, $\theta$ is the diffraction angle, and $\beta_{1/2}$ is the corrected angular full width at half maximum (FWHM) in radians Hindi, 2017$^a$, id.

Lattice Spacing (LS). Bragg's equation was used to calculate LS value as shown below: $LS=n\lambda/2 \sin\theta$, where n is an ordinal number expressed by the value of "1" for diffractograms having the strongest intensity, $\lambda$ is the wavelength of X-rays hit with the crystal (0.1542 nm), and $\theta$ is the Bragg's angle related to the 200-plane, Hindi, 2017$^a$, id.

Fourier Transform Infrared (FTIR) Spectroscopy. The FTIR was used to study the chemical groups of the NCC using a Bruker Tensor 37 FTIR spectrophotometer. The MCC samples were oven-dried at 100° C. for 4-5 h, mixed with KBr in a ratio of 1:200 (w/w) and compressed under vacuum into pellets. The FTIR-spectra were recorded in the transmittance mode in the range of 4000-500 cm$^{-1}$.

Thermal Analysis. Thermogravimetric analyses (TGA) of the NCC were applied by using a Linseis STA PT1000 analyzer. Heating scans were considered from 30 up to 550° C. at 20° C./min in a flowing nitrogen atmosphere for the NCC; Hindi, 2017$^{b,c}$, id.

Statistical Design and Analysis. Completely randomized design with three replications was performed in the present investigation using the analysis of variance procedure and least significant difference test (LSD) at P≤0.05 according to Steel and Torrie (1980). See Steel, R. G. D. and Torrie, T. H. 1980. *Principles and procedures of statistics*, N.Y., USA, incorporated herein by reference in its entirety.

Characterization of the NCC

Microscopic characterization. The NCC produced according to the invention as disclosed was found to extend its crystal growth in an acidic media when a droplet was mounted on a glass substrate up to an urchin-shaped architecture; see FIGS. 2A-2D. For the urchin-shaped NCCs as described by Table 2 and FIG. 1, the centric urchins produced by hot hydrolysis had the highest width of 426.21 µm and the lowest furriness of 70 radius/urchin. On the other hand, the dwarf centric urchins had the lowest width of 70.12 µm and the highest furriness of 700 radius/urchin. In between, the NCCs obtained by hair ice-cold hydrolysis had medium values of width and furriness between the other hydrolysis schemes of 134.2 µm and 320 radius/urchin, respectively. Cryogenic hydrolysis was found to enhance the crystal growth by increasing hydrogen bonds within the CNCs lattice that facilitate their agglomeration into microcrystalline form and subsequent ease collection by ordinary filtration without needing to centrifugation or sonication. This procedure was performed in a sudden cooling conditions that permitted precipitation of the NCC-crystals in a reasonable yield (38.8%) from the microcrystalline cellulose synthesized from leaflets of date palm fronds (*Phoenix dactylifera* L.) discarding both sonication and centrifugation processes.

Figure 4:
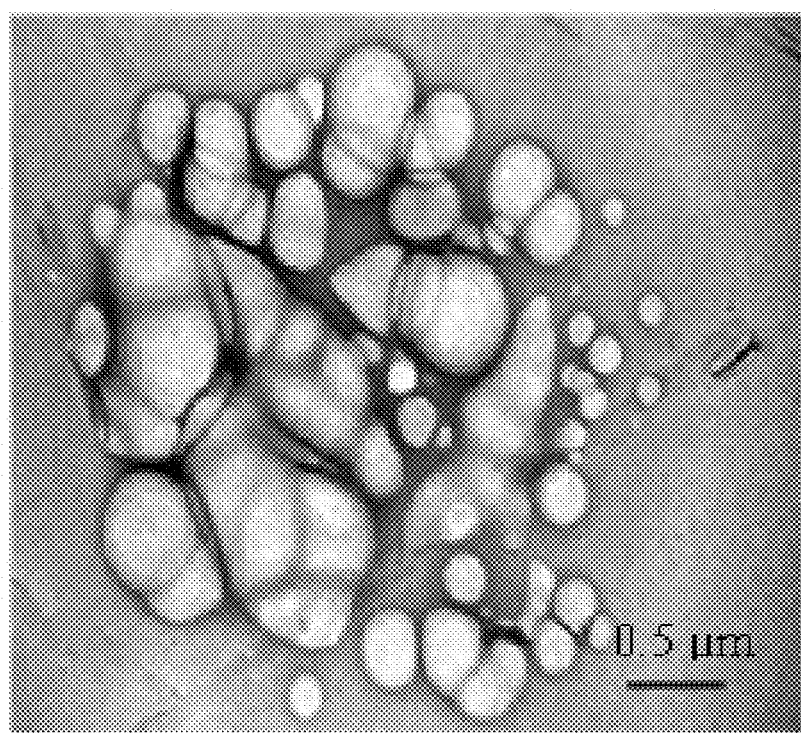
FIG. 4 depicts a TEM micrograph of NCC clusters having various shapes.

SEM micrographs of these structures are shown by FIGS. 3A-3D and a transmission electron micrograph (TEM) is depicted by FIG. 4.

Figure 5:
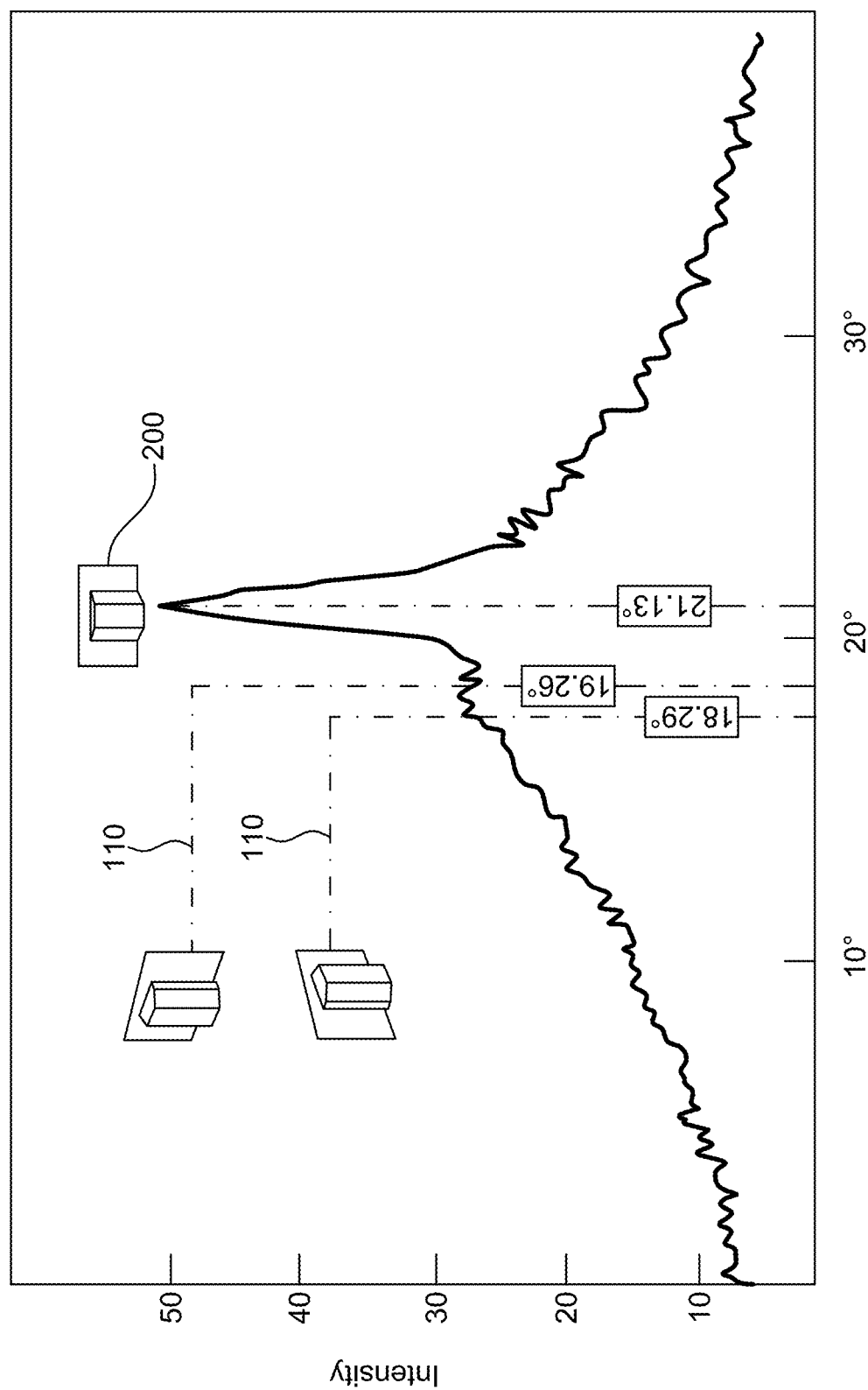
FIG. 5 depicts a X-ray diffractogram of the NCC synthesized as disclosed herein. Boxed values left to right: 18.29°, 19.26° and 21.13°.

X-Ray Diffraction (XRD). It is clear from FIG. 5 that X-rayed NCC exhibited a principle sharp peak around 2θ=21.13° representing the 200 reflection related to the crystalline materials such as hemicelluloses and alpha-cellulose. In addition, the NCC sample showed two broad peaks at 2θ=18.29° and 19.26° representing 110 and 11⁻0 reflections. Accordingly, the similarity between the resultant NCCs and cellulose-I was clear, especially with respect to the crystallographic planes, namely 110, 11⁻0 and 200 as indicated in FIG. 5; see Wada, M., Heux, L., and Sugiyama, J. 2004. *Polymorphism of cellulose I family: Reinvestigation of cellulose IV*. Biomacromolecules, 5: 1385-1391; Chen, W. S., Yu, H. P., Liu, Y. X., Chen, P., Zhang, M. X., and Hai, Y. F. 2011. *Individualization of cellulose nanofibres from wood using high-intensity ultrasonication combined with chemical pretreatments*. Carbohydr. Polym., 83: 1804-1811; Kumar et al. 2014, id., and Hindi, 2017$^{a,b}$, id, each incorporated herein by reference in their entirety.

Crystallinity Index (CI). The CI or crystallinity index of the NCC was found to be high at 86%. This value approaches to that for the MCC precursor. Both materials retained only the crystalline regions of the parent cellulosic microfibrils after removal of the amorphous regions by the method of the invention. The obtained CI was higher than the cellulose and NCC (70.62 and 76.01%, respectively) estimated by Wulandari et al. (2016) or wood pine (70%) determined by Borysiak and Doczekalska (2005), and lies within the CI ranges (41.5% to 95.5%) calculated by Park et al. (2010), id., and approaches to that calculated by Chen et al. (2017), id. See Wulandari, W. T., Rochliadi, A., and Arcana, I. M. 2016. *Nanocellulose prepared by acid hydrolysis of isolated cellulose from sugarcane bagasse.* IOP Conf. Series. Materials Science and Engineering, 107: 012045 doi:10.1088/1757-899X/107/1/012045; Borysiak, S. and Doczekalska, B. 2005. *X-ray diffraction study of pine wood treated with NaOH. Fibers and Textiles in Eastern Europe*, 5 (53): 87-89; Park, S., Baker, J. O., El-Himmell, M., Parilla, P. A., and Johnson, D. K. 2010. *Cellulose crystallinity index: Measurement techniques and their impact on interpreting cellulase performance.* Biotechnology for Biofuels. 3. 10. DOI: 10.1186/1754-6834-3-10; and Chen, Y. W., Tan, T. H., Lee, H. V., and Abd Hamid, S. B. 2017. *Easy fabrication of highly thermal-stable cellulose nanocrystals using $Cr(NO_3)^3$ catalytic hydrolysis system: A feasibility study from macro- to nano-dimensions.* Materials, 10: 42. DOI:10.3390/ma10010042, each incorporated herein by reference in their entirety.

Crystallite Size (CS). The CS is the crystallite thickness estimated by the Scherrer formula for small crystallites with less than 100 nm width. The average CS of the NCC was determined to be 2.8 nm which is similar to that found by Hindi, but smaller than that for cellulose I (about 5 nm in width). This finding agrees with the range estimated by Hindi (2017[a,c] id).

Lattice Spacing (LS). The LS of the NCC is a distance between their successive strata within a crystallite using the Bragg's equation. See Clair, B., Almeras, T., Yamamoto, H., and Okuyama, J. 2006. *Mechanical behavior of cellulose microfibrils in tension wood, in relation with maturation stress generation.* Biophysics Journal, 91 (3): 1128-1137. DOI: 10.1529/biophysj.105.078485, incorporated herein by reference in its entirety. The LS was estimated to be 0.214 nm. Since larger crystal size leads to a larger LS between its strata, the lower LS value can be attributed to the small size of the NCC crystallite estimated in the present invention (2.8 nm). See Davidson, T., Newman, R. H., and Ryan, M. J. 2004. *Variations in the fibre repeat between samples of cellulose I from different sources.* Carbohydrate Research, 339 (18), 2889-2893. DOI: 10.1016/j.carres.2004.10.005, incorporated herein by reference in its entirety. The LS value was slightly smaller than that found by Hindi (2017[a,c], id).

Figure 6:
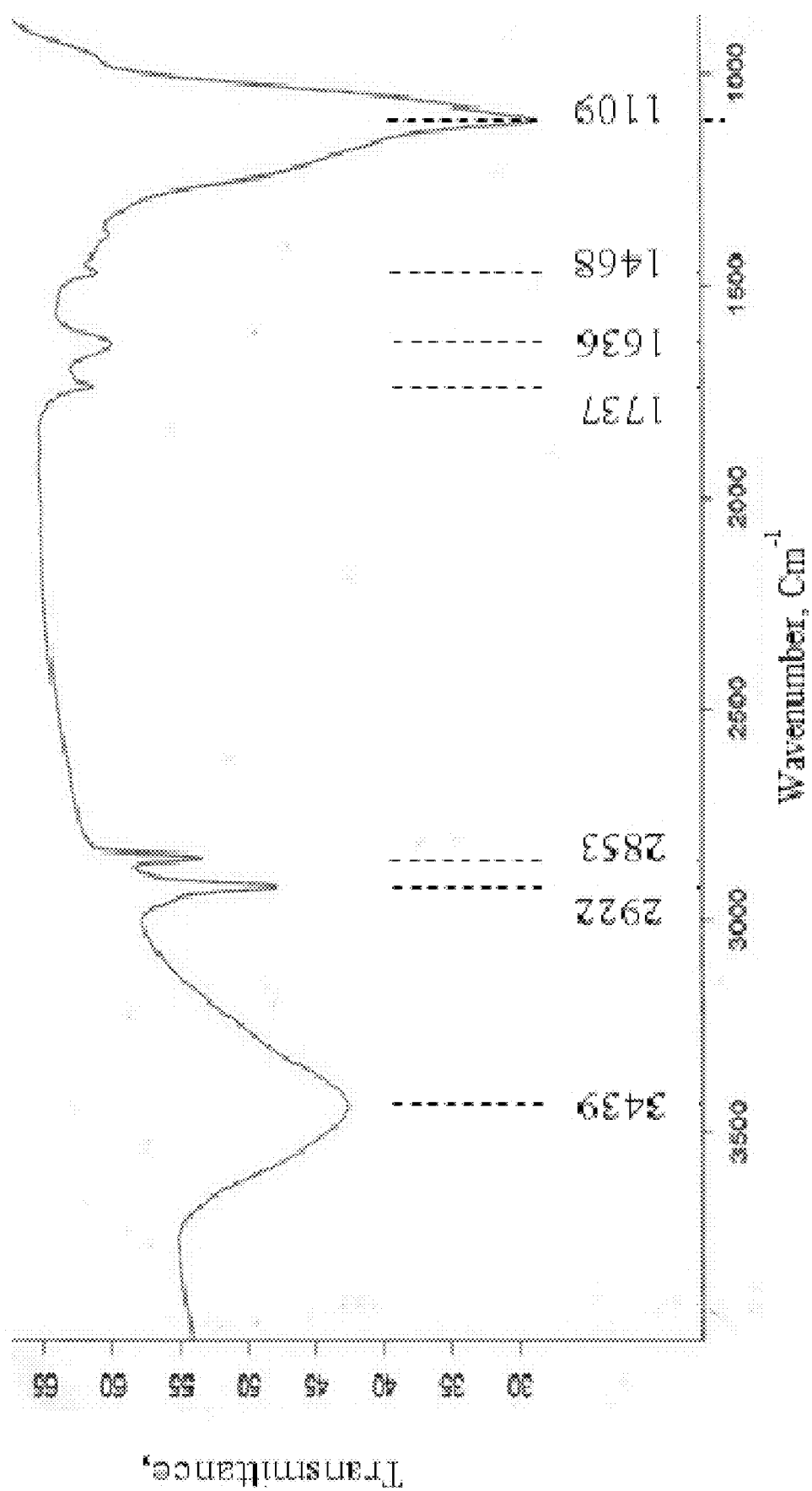
FIG. 6 shows Fourier Transform Infrared (FTIR) spectra of the NCC produced as disclosed herein. Indicated values from left to right: 3439, 2922, 2853, 1737, 1636, 1468 and 1109.

Fourier Transform Infra-Red (FTIR) Spectroscopy. The FTIR characterization is an indicator for any changes in chemical functionality of the MCC precursor via its $H_2SO_4$-hydrolysis to produce NCC; see FIG. 6. The FTIR spectra showed distinct absorption bands of chemical groups of the NCC. All samples presented two main absorbance regions between about 800-1800 $cm^{-1}$ to 2800-3500 $cm^{-1}$. The FTIR spectra of all samples showed sharp bands around the following wavenumbers:

at 1109 $cm^{-1}$ due to C—C ring stretching band (~1155 $cm^{-1}$) and C—O—C glycosidic ether band (1105 $cm^{-1}$) (Kumar et al., 2014; Mandal, Arup, and Debabrata Chakrabarty. *Isolation of nanocellulose from waste sugarcane bagasse (SCB) and its characterization.* Carbohydrate Polymers 86, no. 3 (2011): 1291-1299; Garside, P. and Wyeth, P., 2003. *Identification of cellulosic fibres by PIM spectroscopy-thread and single fibre analysis by attenuated total refectance.* Studies in Conservation, 48(4), pp. 269-275; Nelson, M. L. and O'Connor, R. T., 1964a. *Relation of certain infrared bands to cellulose crystallinity and crystal latticed type. Part I. Spectra of lattice types I, II, III and of amorphous cellulose.* Journal of Applied Polymer Science, 8(3), pp. 1311-1324.

at 1468 $cm^{-1}$ due to scissoring motion of the $CH_2$-group in the NCC (Kumar et al., 2014; Mandal and Chakrabarty. 2011; Garside and Wyeth. 2003; Nelson and O'Connor, 1964[a]; Nelson, M. L. and O'Connor, R. T., 1964. *Relation of certain infrared bands to cellulose crystallinity and crystal lattice tape. Part II. A new infrared ratio for estimation of crystallinity in celluloses I and II.* Journal of Applied Polymer Science, 8(3), pp. 1325-1341;

at 1636 $cm^{-1}$ due to O—H bending of the absorbed water (Kumar et al., 2014; Khalil et al., 2001; Moran et al., 2008; Troedec et al., 2008; Zain et al., 2014; Costa et al., 2015);

at 1737 $cm^{-1}$ due to C—O stretching vibration for the acetyl and ester linkages (Kumar et al., 2014);

at 2853-2922 $cm^{-1}$ due to C—H stretching (Kumar et al., 2014; Khalil et al., 2001; Zain et al., 2014); and at 3439 $cm^{-1}$ due to O—H stretching (axial vibration) intramolecular hydrogen bonds for cellulose I. See Costa, L. A. de S., Fonseca, A. F., Pereira, F. V. and Druzian, J. I. 2015. *Extraction and characterization of cellulose nanocrystals from corn stover.* Cellulose Chem. Technol. 49 (2): 127-133; Dong, X. M., Revol, J. F., Gray, D. 1998. *Effect of microcrystallite preparation conditions on the formation of colloid crystals of cellulose.* Cellulose. 5: 19-32; and Khalil, H., Ismail, H., Rozman, H. and Ahmad, M. 2001. *The effect of acetylation on interfacial shear strength between plant fibres and various matrices.* Eur. Polym 37, 1037-1045; Li, J. et al. 2014. *Homogeneous isolation of nanocellulose by controlling the shearing force and pressure in microenvironment.* Carbohyd. Polym. 113: 388-399; Moran, J. I., Alvarez, V. A., Cyras, V. P., and Vazquez, A., 2008. *Extraction of cellulose and preparation of nanocellulose from sisal fibers*, Cellulose. 15: 149-159; Troedec, M., Sedan, D., Peyratout, C., Bonnet, J., Smith, A., Guinebretiere, R., Gloaguen, V., and Krausz, P. 2008. *Influence of various chemical treatments on the composition and structure of hemp fibers*, Composites Part A-Appl. Sci. Manufact. 39: 514-522; and Zain, N. F. M., Yusop, S. M. and Ishak Ahmad, I. 2014. *Preparation and characterization of cellulose and nanocellulose from pomelo (Citrus grandis) albedo.* Nutr Food Sci. 5:1. doi:10.4172/2155-9600.1000334, each incorporated herein by reference in their entirety.

Based on the spectral results, the inventors confirmed that NCC has a negligible amorphous cellulose content and is composed of crystalline cellulose I, similar to the MCC precursor cellulose.

Figure 7:
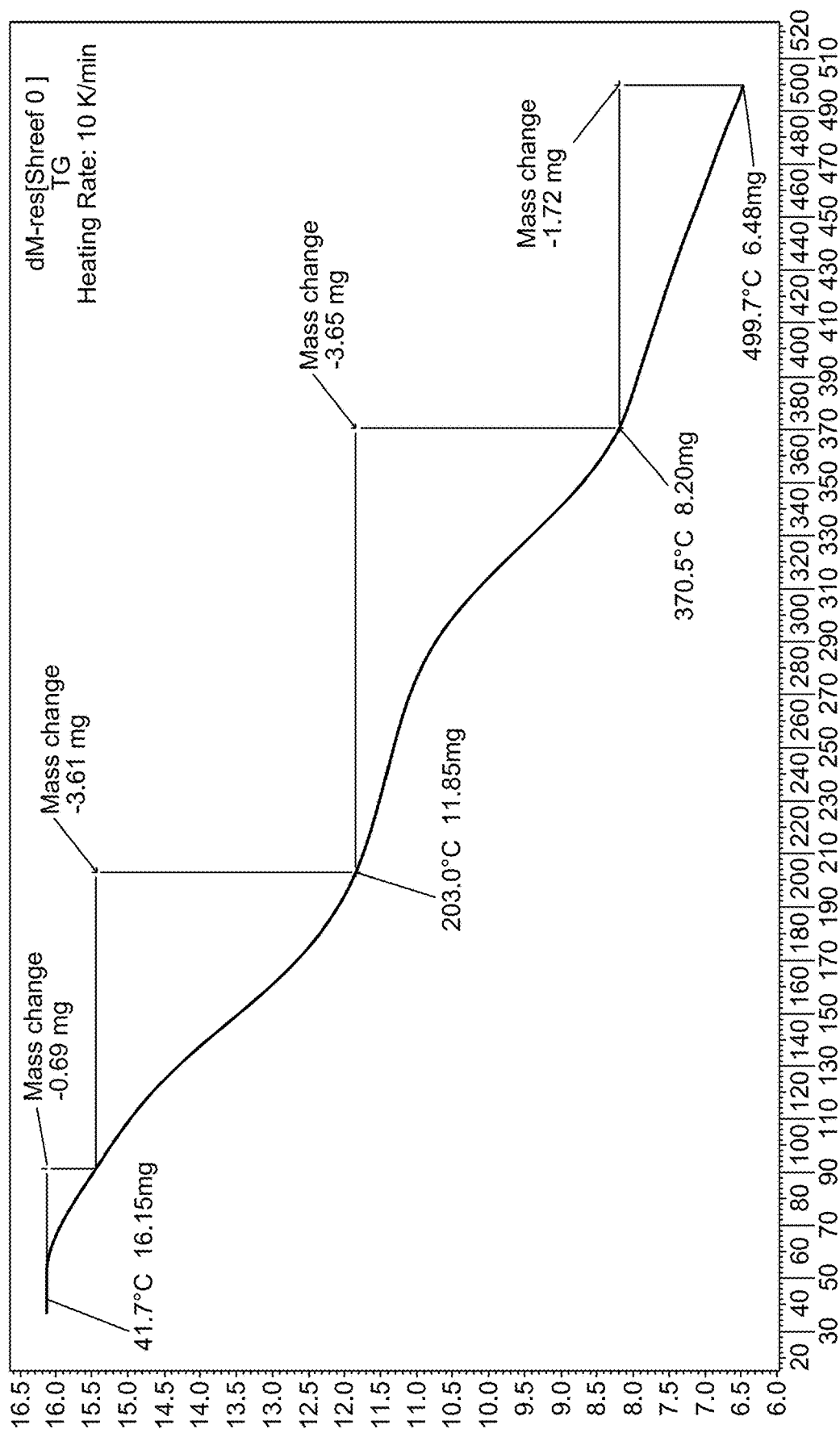
FIG. 7 shows thermogravimetric analysis (TGA) diagram of NCC synthesized according to the method of the invention showing from left to right, mass changes of −0.69 mg, −3.61 mg, −3.65 mg, and −1.72 mg. Y axis scale from 6.0 to 16.5. X axis scale from 20 to 520. Mass change from left to right: −0.69, −3.61, −3.65, and −1.72 mg.

Thermogravimetric Analysis (TGA). The TGA thermogram of the NCC in FIG. 7 showed a gradual increase in their mass loss upon rising temperature from 25° C. up to 500° C. in flowing $N_2$-gas. This range was divided into five separated regions, namely 25-100° C., 100° C.-200° C., 200° C.-300° C., 300° C.-400° C., and 400° C.-500° C. to study the NCC-mass loss occurred at each regime due to the thermal effect. The NCC lost about 5% of its origin weight between 25° C. to 100° C. due to evaporation of free water (Hindi, 2017[b], id.). Furthermore, mass of the NCC was lost by about 22% of their parent mass when the temperature was raised from 100° C. to 200° C. due to evaporation of both hygroscopic and constitutional water. In addition, between 200° C.-300° C., the NCC mass loss was about 12%. With increasing temperature, the NCC continued to lose additional mass as 25% and 17% for the 4th (300° C.-400° C.) and 5th (400° C.-500° C.) regions, respectively. Furthermore, the sulfate groups in sulfated-NCC required less energy to be eliminated (Julien et al., 1993), therefore, $H_2SO_4$-molecules are formed at lower temperatures than those at higher temperatures. See Julien, S., Chomet, E., and Overend, R. P. 1993. *Influence of acid pre-treatment ($H_2SO_4$, HCl, $HNO_3$) on reaction selectivity in the vacuum pyrolysis of cellulose.*

Journal of Analytical and Applied Pyrolysis, 27(1), 25-43, incorporated herein by reference in its entirety.

Differential Thermal Analysis (DTA). DTA is a measuring tool to differentiate two hot materials. Here, the first one is the NCC and the second one is an inert reference material. Both materials are found at the same place and conditions. As shown in FIG. 8, there was an endothermic peak found under the baseline and one exothermic peak present above this line. The endothermic peak begins from 40° C. up to 270° C. with a maximum shift at 150° C., while the exothermic peak starts from 270° C. until 450° C. with a maximum value at 340° C.; see FIG. 8 and Table 1.

The endotherm of the DTA thermogram can be attributed to evaporation of the three forms of moisture content in the NCCs—free, hygroscopic and constitutional moisture—besides fusion or melting process of the NCC. For the sulfated NCC, the hydrolyzing agent used was $H_2SO_4$ that acted as a dehydrating agent helping for grafting the hydrophobic sulfate groups that lowering their moisture affinity. Accordingly, after the acid hydrolysis of the MCC, only nanoscale cellulose crystals would possess the sulfate groups responsible for the higher onset temperature of crystal melting with wider endotherm.

The exotherm can be attributed to the depolymerization of the sulfated NCC, decomposition of glycosyl units and then formation of carbonaceous particles (Kumar et al., 2014). This depolymerization can be attributed to four effects: (a) the nanosize and the huge number of the free ends of the NCC-chains which were decomposed at lower temperatures, (b) $H_2SO_4$ that is a dehydrating agent that facilitates the depolymerization of NCC by elimination of some hydroxyl groups, (c) the presence of $H^+$ protons in the weak acidic atmosphere which may be responsible on increasing the carbonaceous residues, and (d) the highly crystalline nature of the NCC increased in the carbonaceous residues. See Wada et al., 2004, and George, J Ramana, K. V., Bawa, A. S., and Siddaramaiah. 2011. *Bacterial cellulose nanocrystals exhibiting high thermal stability and their polymer nanocomposites*. Internl. J. Biologic. Macromol., 48: 50-57, each incorporated herein by reference in their entirety.

As mentioned above, the NCC produced by the method of the invention was found to extend its crystal growth, in an acidic media when a droplet was mounted on a glass substrate, up to a urchin-shaped architecture. The X-rayed NCC exhibited a principle sharp peak around 2θ=21.13° representing the 200 reflection related to the crystalline materials (hemicelluloses and alpha-cellulose) as well as two broad peaks at 2θ=18.29° and 19.26° representing 110 and 11— 0 reflections. This shows the high similarity between the resultant NCC and cellulose-I, especially when regarding the crystallographic planes, namely 110, 11— 0 and 200. For the thermogravimetric thermogram of the NCC, there is an endothermic peak found under the baseline, while one exothermic peak is present above this line. The thermogravimetric thermogram of the NCC showed a gradual increase in their mass loss upon rising temperature from 25° C. up to 500° C. in a flowing $N_2$ gas.

In addition, the absolute value of the heat change for the endotherms was estimated to be 639 μVs/mg that is extremely higher than that the exotherm (37 μVs/mg). Since the material absorbing higher energy are more thermally stable than those absorbing lower energy or releasing more energy (Hindi, et al, 2017), the NCC have excellent thermal stability.

TABLE 1

Differential thermal analysis (DTA) for temperature range (TR), maximum temperature (MT) and enthalpy change (EC) of the nanocrystalline cellulose (NCC) upon thermal degradation up to 500° C.

| Thermogram | | TR | MT | EG |
|---|---|---|---|---|
| No | type | (° C.) | (° C.) | (μVs/mg) |
| 1 | Endotherm | 40-270 | 150 | −640 |
| 2 | Exotherm | 270-450 | 340 | 38 |

TABLE 2

Comparison of conventional NCC production with the Example

| | Cellulose Nanocrystal (CNC) production | |
|---|---|---|
| Source of variation | Conventional Methods | Example (invention) |
| Using sulfuric acid | Used | Used |
| Sulfuric acid concentration (wt/wt) | 60-64% | 98.06% |
| Acid/cellulose ratio | 8:1 | 1:1 |
| Hydrolysis temperature | 50-100° C. | Cooling to 10° to 15° C. with fine water ice granules |
| Sonication | Used | Not Used |
| Centrifugation | Used | Not Used |
| Crystals isolation | Immediately after centrifugation | production of nanosized crystals filtration |
| Batch duration* | 4 hours | 10 minutes |
| NCC yield | 8-20 wt % | 60 wt % based on weight of the MCC precursor |

*The time consumed from adding acid up to obtaining the weight unity of cellulose nanocrystals.

As apparent from the comparison above in Table 2, the method of the invention provides a fast and simple production scheme for NCC which can be performed without complex requiring instruments such as centrifuges or sonicators. The use of simple separation steps to recover NCC, such as use of filter paper or sinter glass filters and Gooch filtration, eliminates the need for these devices simplifies production and reduces equipment and maintenance costs. The method of the invention also reduces the amount of sulfuric acid needed by conventional processes further reducing costs. Moreover, it is unnecessary to prewet a cellulosic substrate prior to contacting it with concentrating sulfuric acid.

Use of a flash-hydrolysis method according to the invention provides hydrolysis within a narrow temperature range, such as between 10° C. and 15° C. and is quenched with the addition of inexpensive and non-toxic water and water ice. Degradation of MCC once treated with the concentrated sulfuric acid was minimized or eliminated in the presence of frozen sulfuric acid. Moreover, the inventors found that crystal size of the NCC could be controlled by simply adjusting the temperature of either the hydrolysis or subsequent separation (e.g., filtration) of the NCC.

The method of the invention provides for a highly pure NCC substantially free of amorphous cellulosic regions and an NCC product that retains Cellulose I structure despite treatment with concentrated sulfuric acid. Moreover, the method of the invention provides for grafting or up to three sulfate groups onto the available carbon sites (no's 3, 4, and 6) of the glucopyranose unit constituting the cellulose chain. A high content of grafted sulfate groups can generate high electrostatic charges in the resulting NCC product.

The properties and advantages described herein provide a method that can be industrially scaled to produce large quantities of NCC at a low cost.

Example 2

Characterization of NCC Synthesized Using Three Different Hydrolysis Schemes

NCC was produced by the method of the invention and by conventional hot hydrolysis and cryogenic cold hydrolysis. The NCC product of the present invention prepared using hair ice-cold hydrolysis was characterized by optical microscopy, X-Ray Diffraction (XRD) as well as Fourier Transform Infrared (FTIR) Spectroscopy and then compared to NCC product synthesized by the traditional method of hot hydrolysis and cryogenic cold hydrolysis.

The Optical Vision System. The optical speculation unit used consisted of a light microscope (CE-MC200A) in a magnification power of 10× with suitable vision system (OPTIKA PRO 5 Digital Camera-4083.12) using a Vision PRO 4 software to pick up and process images as well as to record different measurements of the cellular dimensions in a micrometer scale. In addition, the software was also used to show the light intensity of the images.

It was found that different nanocrystalline cellulose (NCCs) constructions, which were termed as urchins, were formed upon crystal growth in an acidic media on a glass slide. The difference between the urchins depended on the cooling procedure used through the hydrolysis scheme applied.

TABLE 3

Mean values[1] for width and furriness of the urchins produced by the three hydrolysis schemes upon a droplet shrinking on a glass slide in an acidic media.

| Hydrolysis scheme | Width (µm) | Furriness (radius/urchin) |
|---|---|---|
| Hot hydrolysis[2] | 426.21[A] | 70[C] |
| Hair ice-cold hydrolysis[3] | 134.2[B] | 320[B] |
| Cryogenic-cold hydrolysis[4] | 70.12[C] | 700[A] |

[1]Means with the different letter at the same column are differed significantly at 5% Level.
[2]Hindi, 2017[d].
[3]The present invention.
[4]Hindi and Abohassan, U.S. patent application 20170291962.

Figure 2B:
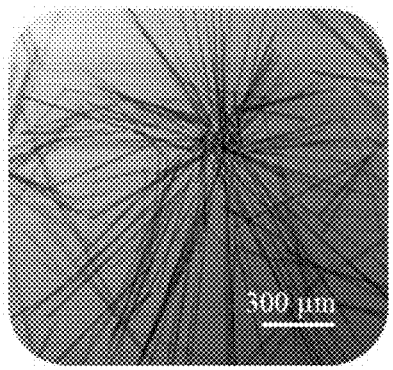
FIG. 2B. Large NCC urchins produced by hot hydrolysis.
Figure 2C:
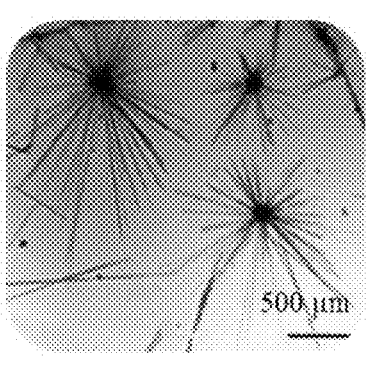
FIG. 2C. Medium NCC urchins produced by hair-ice cold hydrolysis.
Figure 2D:
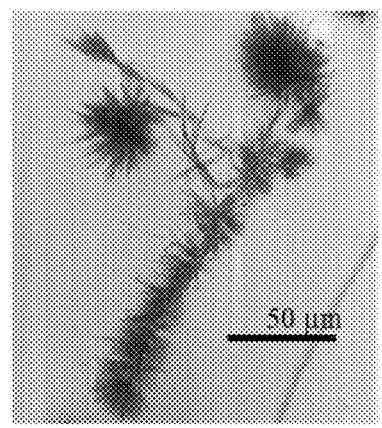
FIG. 2D. Dwarf NCC urchins produced by cryogenic-cold hydrolysis.

FIGS. 2B-2D show different urchin shaped constructions synthesized by the three hydrolysis schemes. In FIG. 2B large urchins were synthesized by hot hydrolysis and in FIGS. 2C and 2D dwarf urchins synthesized by cryogenic acid hydrolysis.

As described above, for the urchin-shaped NCCs described in Table 3 and FIGS. 2B-2D, the centric urchins produced by hot hydrolysis had the greatest width of 426.21 µm and the lowest furriness of 70 radius/urchin. On the other hand, the dwarf centric urchins had the lowest width of 70.12 µm and the highest furriness of 700 radius/urchin. In between, the NCCs obtained by hair ice-cold hydrolysis had medium values of width and furriness between the other hydrolysis schemes, namely 134.2 µm and 320 radius/urchin, respectively.

The inventors found that cryogenic hydrolysis enhanced the crystal growth by increasing hydrogen bonds within the CNCs lattice that facilitated agglomeration into a microcrystalline form and subsequently facilitated collection by ordinary filtration without centrifugation or sonication. This procedure was performed under sudden cooling conditions that permitted precipitation of the NCC crystals in a reasonable yield of 38.8% from the microcrystalline cellulose synthesized from leaflets of date palm fronds (*Phoenix dactylifera* L.) without sonication or centrifugation.

XRD. The XRD spectra of the fibers were used to study sample crystallinity using the XRD-D2 Phaser Bruker (USA). The generator was operated at 30 KV and 30 mA. The samples were exposed for a period of 3000 s using CuKa radiation with a wavelength of 0.15418 nm. The sample crystallinity is defined as the ratio of the amount of crystalline cellulose to the total amount of sample material including crystalline and amorphous segments. All the experiments were performed in the reflection mode at a scan speed of 4°/min in steps of 0.05°. All samples were scanned in a 2θ=26° range varying from 4° to 30°; see Hindi, S. S. Z. 2017[a], *Microcrystalline cellulose: The inexhaustible treasure for pharmaceutical industry*. Nanoscience and Nanotechnology Research. 4 (1): 22-31. 10.12691/nnr-4-1-3; Hindi, S. S. Z. 2017[b]. *Differentiation and Synonyms Standardization of Amorphous and Crystalline Cellulosic Products*. Nanoscience and Nanotechnology Research. 2017; 4(3):73-85. doi: 10.12691/nnr-4-3-1.

The XRD pattern showed a principle sharp peak around two theta of about 22.6° for the three hydrolysis schemes which are supposed to represent the typical cellulose-I structure. The nanocellulosic crystals exhibited characteristic assignments of 110, 200, and 004 planes, respectively; Wada, M., Heux, L., and Sugiyama, J. 2004. *Polymorphism of cellulose I family: Reinvestigation of cellulose IV.* Biomacromolecules. 5: 1385-1391; Chen, W. S., Yu, H. P., Liu, Y. X., Chen, P., Zhang, M. X., and Hai, Y. F. 2011. *Individualization of cellulose nanofibres from wood using high-intensity ultrasonication combined with chemical pretreatments*. Carbohydr. Polym. 83: 1804-1811; Kumar, S., Saha, T., Sharma, S. 2015. *Treatment of pulp and paper mill effluents using novel biodegradable polymeric flocculants based on anionic polysaccharides: a new way to treat the waste water*. Int Res J Eng Technol. 2 (4):1-14). The XRD analyses revealed that the NCCs had the same crystalline structure of cellulose-I.

Crystallinity Index. Individual crystalline peaks were first extracted by a curve-fitting process from the diffraction intensity profiles. The CI was calculated by dividing the diffractogram area of crystalline cellulose by the total area of the original diffractogram. The area under the curve was estimated by summing of adjacent trapezoids using Excel (Microsoft, USA) as described by Hindi, S. S. Z. 2017[c]; *Some Promising Hardwoods for Cellulose Production: I. Chemical and Anatomical Features. Nanoscience and Nanotechnology Research.* 2017; 4(3):86-97. doi: 10.12691/nnr-4-3-2.). The crystallinity index of the NCCs synthesized by hot hydrolysis (85.9%) was higher than those synthesized by hair ice-cold hydrolysis (82.6%), and cryogenic hydrolysis (80.2%).

Crystallite Size (CS). The CS is the NCCs crystallite thickness (nm) determined by the Scherrer equation when the crystals are smaller than 100 nm; Ciupina, V., Zamfirescu, S., and Prodan, G. 2007. *Evaluation of mean diameter values using Scherrer equation applied to electron diffraction images*, In: Nanotechnology-Toxicological Issues and Environmental Safety, NATO Science for Peace and Security Series, 231-237. DOI: 10.1007/978-1-4020-6076-2_15. The CS was calculated with respect to the crystallographic plane, namely 002 as follows: $CS = K\lambda/\beta_{1/2} \cos\theta$, where K is the correction factor and usually taken to be 0.91, λ is the radiation wavelength, θ is the diffraction angle, and $\beta_{1/2}$ is the corrected angular full width at half maximum (FWHM) in radians; Hindi, S. S. Z. 2017$^c$, Some Promising Hardwoods for Cellulose Production: I. Chemical and Anatomical Features. Nanoscience and Nanotechnology Research. 2017; 4(3):86-97. doi: 10.12691/nnr-4-3-2). The average crystallite size of the NCCs didn't significantly differ due to the cellulosic product although there was a descending trend from the hot up to the cryogenic hydrolysis (Table 3).

Lattice spacing (LS). The averages LS of the NCCs didn't differ significantly due to the cellulosic product although there is a descending trend from the hot up to the cryogenic hydrolysis (Table 3).

TABLE 4

Main values of the important crystallographic properties of the NCCs synthesized by the three hydrolysis schemes.

| Hydrolysis scheme | Crystallinity Index, % | Crystallite size nm | Lattice spacing nm |
|---|---|---|---|
| Hot hydrolyzed[2] | 85.9 (1.094)[1] | 2.99 (0.142) | 0.202 (0.014) |
| Hair ice-cold hydrolyzed[3] | 82.6 (0.984) | 2.42 (0.098) | 0.273 (0.057) |
| Cryogenic-cold hydrolyzed[4] | 80.2 (1.297) | 2.15 (0.131) | 0.298 (0.063) |

[1]Standard deviation
[2]Hindi, 2017$^d$.
[3]the present invention.
[4]Hindi and Abohassan patent.

FTIR Spectroscopy. The FTIR was used to investigate chemical structure of the NCCs samples using a Bruker Tensor 37 FTIR spectrophotometer. The samples were oven-dried at 100° C. for 4-5 h, mixed with KBr in a ratio of 1:200 (w/w) and pressed under vacuum to form pellets. The FTIR-spectra of the samples were recorded in the transmittance mode in the range of 4000-500 cm$^{-1}$.

As reviewed by Hindi, S. S. Z. 2017$^d$. Suitability of date palm leaflets for sulphated cellulose nanocrystals synthesis. Nanoscience and Nanotechnology Research, 2017, Vol. 4, No. 1, 7-16. DOI:10.12691/nnr-4-1-2, changes in chemical functionality after $H_2SO_4$-hydrolysis of the leaflets of date palm were obtained by FTIR spectroscopy. The spectra of the resultant NCCs synthesized by the three hydrolysis schemes showed absorption bands of chemical groups characteristic of the crystalline product. All samples presented two main absorbance regions in the range of about 800-1800 cm$^{-1}$ to 2800-3500 cm$^{-1}$. The FTIR spectra of all samples have shown sharp bands around the following wavenumbers:

1108.46 cm$^{-1}$ due to C—C ring stretching band (~1155 cm$^{-1}$) and C—O—C glycosidic ether band (1105 cm$^{-1}$).

1467.21 cm$^{-1}$ due to scissoring motion of the $CH_2$-group in the SCNCs.

1635.13 cm$^{-1}$ due to O—H bending of the absorbed water.

1737.31 cm$^{-1}$ due to C—O stretching vibration for the acetyl and ester linkages.

2852.45-2921.49 cm$^{-1}$ due to C—H stretching.

3438.08 cm$^{-1}$ due to O—H stretching (axial vibration) intramolecular hydrogen bonds for cellulose I.

Based on the spectral data, it can be confirmed that the NCCs synthesized by the three hydrolysis schemes are composed of crystalline cellulose I while content of amorphous cellulose is negligible.

Example 3

Production of Hair-Shaped Ice.

Massive ice preparation. Using a deep freezer maintained at −32° C. for 6 hours, distilled water in a suitable stainless steel containers (660 ml) was frozen.

Ice lumps preparation. A crusher was used to fracture the massive ice into smaller pieces or ice lumps having a mean diameter of about 4 cm.

Hair-shaped ice isolation. Using a precooled-high speed mixer with very thin and sharp knives, the ice lumps were cut into smaller particles about 1 mm in diameter. The about 1 mm-ice particles were sieved to exclude excess free water and provide a homogeneous ice particle size. The 1 mm ice particles were mildly compressed in a manual compressor in a stainless steel capsule for 1 minute at a compression pressure of 30 psi under cooling at 0° C. in an isolated atmosphere to form icy scales (3 mm longitudinally, 1 mm radially, and 1 mm tangentially). The pressure was maintained using a screw system and the capsule was cooled for 15 min at −32° C. Splitting the icy scales into icy hairs. The automated compressor using interlocked knives—movable knives alternated with stationary ones—and fixed between the two boards of the compressor was used to form the hair shape ice to about 3 mm in length, and 1 mm in width. The compression process excludes free water with an aim of cold vacuum filtration. The dehydrated hair-shaped ice refers to ice granules free of any free water surrounding their particles. This elimination of the free water can be done by vacuum-cold filtration. The vacuum aid is necessary to exclude the existent free water rapidly, while the cooling aid is essential to prevent melting ice to produce excess of free water. In addition, the cooling process freezes the hygroscopic water films enveloping the ice particles. This is due to that heat enthalpy of the free and hygroscopic water is higher than that of the ice itself. Accordingly, the obtained hair ice has the maximum cooling ability comparing to other forms of water ice.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. Urchin shaped nanocrystalline cellulose (NCC) having an average degree of polymerization from 1,000 to about 1,500 and that exhibits a cellulose I structure,
    wherein the NCC includes glucopyranose units grafted with one or more sulfate groups;
    wherein the NCC is made by a method comprising:
        contacting frozen concentrated sulfuric acid with microcrystalline cellulose ("MCC") to form a mixture, and holding the mixture at a hydrolysis temperature ranging from about 10° C. to 15° C. for a time sufficient to form a cellulosic paste containing hydrolyzed MCC,
        diluting the cellulosic paste containing hydrolyzed MCC in a mixture comprising liquid water and water ice to form precipitated NCC, and
        separating the precipitated NCC, thus making the NCC, wherein the frozen concentrated sulfuric acid has a concentration of at least 95 mass %; and
    wherein the NCC is in the form of urchins having a medium width of 134.2 µm.

2. The nanocrystalline cellulose of claim 1, wherein the method of making the NCC, the MCC is in the form of precooled cellulosic fibers at a temperature of less than 25° C.

3. The nanocrystalline cellulose of claim 1, wherein the method of making the NCC, the concentrated sulfuric acid has a concentration of about 98.06 mass % and the cellulosic paste is white.

4. The nanocrystalline cellulose of claim 1, wherein the method of making the NCC, the contacting and diluting occurs at a temperature ranging from 10° C. to 15° C.

5. The nanocrystalline cellulose of claim 1, wherein the method of making the NCC, the contacting occurs at a wt/wt ratio of sulfuric acid to MCC of 2:1 to 1:2.

6. The nanocrystalline cellulose of claim 1, wherein the method of making the NCC, the diluting occurs at a ratio of liquid water and water ice to MCC of 2:1 to 1:2 (wt/wt).

7. The nanocrystalline cellulose of claim 1, wherein the method of making the NCC, the separating is performed by filtering.

8. The nanocrystalline cellulose of claim 1, wherein the method of making the NCC, the separating is performed by filtering, wherein the filtering is performed at a temperature ranging from 0° C. to 15° C.

9. The nanocrystalline cellulose of claim 1, wherein the method of making the NCC further comprises washing the separated NCC with water to increase the pH of the NCC.

10. The nanocrystalline cellulose of claim 1, wherein the method of making the NCC further comprises washing the separated NCC with water to increase the pH of the NCC to pH 6.5 to pH 7.5.

11. The nanocrystalline cellulose of claim 1, wherein the method of making the NCC, the separated NCC is washed with water to increase the pH of the NCC to pH 6.5 to pH 7.5, the method further comprising drying the washed NCC.

12. The nanocrystalline cellulose of claim 1, wherein the method of making the NCC, the MCC is contacted directly with the frozen concentrated sulfuric acid without addition of water or pre-wetting of the MCC and wherein the NCC is produced without sonication or ultrasonic processing and without centrifugation.

13. The nanocrystalline cellulose of claim 1, wherein the urchins have a mean furriness of 320 radius/urchin.

14. The nanocrystalline cellulose of claim 1, having a crystallinity index of 82.6±1%.

15. The nanocrystalline cellulose of claim 1, having a crystallite size of 2.42±0.024 nm.

16. The nanocrystalline cellulose of claim 1, comprising cellulose chains having glucopyranose units bonded to three sulfate groups.

* * * * *